United States Patent
Kilian et al.

(10) Patent No.: US 8,722,359 B2
(45) Date of Patent: May 13, 2014

(54) GENES FOR ENHANCED LIPID METABOLISM FOR ACCUMULATION OF LIPIDS

(75) Inventors: Oliver Kilian, Alameda, CA (US); Bertrand Vick, Oakland, CA (US)

(73) Assignee: Aurora Algae, Inc., Hayward, CA (US)

( * ) Notice: Subject to any disclaimer, the term of this patent is extended or adjusted under 35 U.S.C. 154(b) by 163 days.

(21) Appl. No.: 13/011,809

(22) Filed: Jan. 21, 2011

(65) Prior Publication Data

US 2012/0190115 A1 Jul. 26, 2012

(51) Int. Cl.
*C12N 1/12* (2006.01)
*C12N 1/13* (2006.01)
*C12P 1/00* (2006.01)
*C12P 7/64* (2006.01)

(52) U.S. Cl.
USPC ........ 435/41; 435/134; 435/257.1; 435/257.2

(58) Field of Classification Search
None
See application file for complete search history.

(56) References Cited

U.S. PATENT DOCUMENTS

| | | | |
|---|---|---|---|
| 1,926,780 A | 9/1933 | Lippincott | |
| 3,468,057 A | 9/1969 | Buisson et al. | |
| 3,962,466 A | 6/1976 | Nakabayashi | |
| 4,003,337 A | 1/1977 | Moore | |
| 4,267,038 A | 5/1981 | Thompson | |
| 4,365,938 A | 12/1982 | Warinner | |
| 4,535,060 A | 8/1985 | Comai | |
| 4,658,757 A | 4/1987 | Cook | |
| 5,105,085 A | 4/1992 | McGuire et al. | |
| 5,478,208 A | 12/1995 | Kasai et al. | |
| 5,527,456 A | 6/1996 | Jensen | |
| 5,661,017 A | 8/1997 | Dunahay et al. | |
| 5,668,298 A | 9/1997 | Waldron | |
| 5,723,595 A | 3/1998 | Thompson et al. | |
| 5,823,781 A | 10/1998 | Hitchcock et al. | |
| 6,027,900 A | 2/2000 | Allnutt et al. | |
| 6,117,313 A | 9/2000 | Goldman et al. | |
| 6,143,562 A | 11/2000 | Trulson et al. | |
| 6,166,231 A | 12/2000 | Hoeksema | |
| 6,297,054 B1 | 10/2001 | Maliga et al. | |
| 6,372,460 B1 | 4/2002 | Gladue et al. | |
| 6,448,055 B1 | 9/2002 | Shimizu et al. | |
| 6,736,572 B2 | 5/2004 | Geraghty | |
| 6,750,048 B2 | 6/2004 | Ruecker et al. | |
| 6,831,040 B1 | 12/2004 | Unkefer et al. | |
| 6,871,195 B2 | 3/2005 | Ryan et al. | |
| 7,244,609 B2 | 7/2007 | Drocourt et al. | |
| 7,381,326 B2 | 6/2008 | Haddas | |
| 7,410,637 B2 | 8/2008 | Sayre et al. | |
| 7,449,568 B2 | 11/2008 | Fukuda et al. | |
| 7,547,551 B2 | 6/2009 | Schuler et al. | |
| 8,039,230 B2 | 10/2011 | Otte et al. | |
| 8,119,859 B2 | 2/2012 | Vick et al. | |
| 8,314,228 B2 | 11/2012 | Kilian et al. | |
| 8,318,482 B2 | 11/2012 | Vick et al. | |
| 2003/0049720 A1 | 3/2003 | Hoshino et al. | |
| 2003/0140021 A1 | 7/2003 | Ryan et al. | |
| 2003/0143743 A1 | 7/2003 | Schuler et al. | |
| 2003/0199490 A1 | 10/2003 | Antoni-Zimmermann et al. | |
| 2003/0211089 A1 | 11/2003 | Sayre et al. | |
| 2004/0161364 A1 | 8/2004 | Carlson | |
| 2004/0262219 A1 | 12/2004 | Jensen | |
| 2005/0064577 A1 | 3/2005 | Berzin | |
| 2005/0095569 A1 | 5/2005 | Franklin | |
| 2005/0124010 A1 | 6/2005 | Short et al. | |
| 2005/0170479 A1 | 8/2005 | Weaver et al. | |
| 2005/0181345 A1 | 8/2005 | Bradbury et al. | |
| 2005/0260553 A1 | 11/2005 | Berzin | |
| 2006/0031087 A1 | 2/2006 | Fox et al. | |
| 2006/0044259 A1 | 3/2006 | Hotelling et al. | |
| 2006/0045750 A1 | 3/2006 | Stiles | |
| 2006/0101535 A1 | 5/2006 | Forster et al. | |
| 2006/0122410 A1 | 6/2006 | Fichtali et al. | |
| 2006/0155558 A1 | 7/2006 | Corpening | |
| 2006/0166243 A1 | 7/2006 | Su et al. | |
| 2006/0166343 A1 | 7/2006 | Hankamer et al. | |
| 2006/0192690 A1 | 8/2006 | Philipp | |
| 2007/0178451 A1 | 8/2007 | Deng et al. | |
| 2008/0118964 A1 | 5/2008 | Huntley et al. | |
| 2008/0120749 A1 | 5/2008 | Melis et al. | |
| 2008/0160488 A1 | 7/2008 | Younkes et al. | |
| 2008/0160591 A1 | 7/2008 | Willson et al. | |
| 2008/0194029 A1 | 8/2008 | Hegemann et al. | |
| 2008/0268539 A1 | 10/2008 | Singh et al. | |
| 2008/0293132 A1 | 11/2008 | Goldman et al. | |
| 2009/0029445 A1 | 1/2009 | Eckelberry et al. | |

(Continued)

FOREIGN PATENT DOCUMENTS

| | | |
|---|---|---|
| CN | 1627764 | 6/2005 |
| CN | 1867140 | 11/2006 |

(Continued)

OTHER PUBLICATIONS

Dunahay et al 1996 Applied Biochemistry and Biotechnology 57/57: p. 223-231.*

Molnar et al. Highly specific gene silencing by artificial microRNAs in the unicellular alga *Chlamydomonas reinhardtii*. Plant Jour. ePub Jan. 17, 2009 vol. 58 No. 1 pp. 157-164. Especially abstract.

Chen et al. Conditional Production of a Functional Fish Growth Hormonal in the Transgenic Line of *Nannochloropsis oculata* (Eustigmatophyceae). J. Phycol. Jun. 2008 vol. 44 No. 3 pp. 768-776. Especially abstract.

(Continued)

*Primary Examiner* — Brent T Page
*Assistant Examiner* — Matthew Keogh
(74) *Attorney, Agent, or Firm* — Carr & Ferrell LLP

(57) ABSTRACT

Provided herein are exemplary genes, constructs and methods for the formation of triacylglycerols (TAGs). The exemplary genes include a phosphatic acid phosphohydrolase (PA Hydrolase) gene, a diacylglycerol o-acyltransferase (DAGAT2A) gene, and a phospholipid:diacylglycerol acyltransferase (LROI) gene.

13 Claims, 6 Drawing Sheets

(56) References Cited

U.S. PATENT DOCUMENTS

| | | |
|---|---|---|
| 2009/0061493 A1 | 3/2009 | Trimbur et al. |
| 2009/0061928 A1 | 3/2009 | Lee et al. |
| 2009/0148931 A1 | 6/2009 | Wilkerson et al. |
| 2009/0234146 A1 | 9/2009 | Cooney et al. |
| 2009/0317857 A1 | 12/2009 | Vick et al. |
| 2009/0317878 A1 | 12/2009 | Champagne et al. |
| 2009/0317904 A1 | 12/2009 | Vick et al. |
| 2009/0319338 A1 | 12/2009 | Parks et al. |
| 2009/0325270 A1 | 12/2009 | Vick et al. |
| 2010/0068772 A1 | 3/2010 | Downey |
| 2010/0100520 A1 | 4/2010 | Dargue et al. |
| 2010/0198659 A1 | 8/2010 | Meltzer et al. |
| 2010/0210003 A1 | 8/2010 | King et al. |
| 2010/0210832 A1 | 8/2010 | Kilian et al. |
| 2010/0314324 A1 | 12/2010 | Rice et al. |
| 2010/0323387 A1 | 12/2010 | Bailey et al. |
| 2010/0330643 A1 | 12/2010 | Kilian et al. |
| 2011/0015415 A1 | 1/2011 | Singh et al. |
| 2011/0059495 A1 | 3/2011 | Bailey et al. |
| 2011/0091977 A1 | 4/2011 | Kilian et al. |
| 2012/0190115 A1 | 7/2012 | Kilian et al. |
| 2013/0102040 A1 | 4/2013 | Radakovits et al. |
| 2013/0131330 A1 | 5/2013 | Kilian et al. |

FOREIGN PATENT DOCUMENTS

| | | |
|---|---|---|
| CN | 1956335 | 5/2007 |
| CN | 101289659 | 10/2008 |
| WO | 2004106238 A2 | 12/2001 |
| WO | 2007084078 | 7/2007 |
| WO | 2008060571 A2 | 5/2008 |
| WO | 2008106803 A1 | 9/2008 |
| WO | 2008060571 A3 | 11/2008 |
| WO | 2008060571 A8 | 2/2009 |
| WO | 2009124070 A1 | 10/2009 |
| WO | 2009149470 A1 | 12/2009 |
| WO | 2010011335 A1 | 1/2010 |
| WO | 2011011463 A2 | 1/2011 |
| WO | 2011049995 A1 | 4/2011 |

OTHER PUBLICATIONS

Nelson et al. Targeted Disruption of the NIT8 Gene in *Chlamydomonas reinhardtii*. Mol. Cell Bio. Oct. 1995, vol. 15, No. 10, pp. 5762-5769. Especially abstract and p. 5763 left col. para 2.
Prein et al., "A Novel Strategy for Constructing N-terminal Chromosomal Fusions to Green Fluorescent Protein in the Yeast *Saccharomyces cerevisiae*," FEBS Letters 485 (2000) 29-34.
Wendland et al., "PCR-Based Methods Facilitate Targeted Gene Manipulations and Cloning Procedures," Curr. Gen. (2003) 44: 115-123.
Kindle, et al., "Stable Nuclear Transformation of *Chlamydomonas* Using the *Chlamydomonas* Gene for Nitrate Reductase," The Journal of Cell Biology 109(6, part 1): 2589-2601.
Endo et al., "Inactivation of Blasticidin S by *Bacillus cereus* II. Isolation and Characterization of a Plasmid, pBSR 8, From *Bacillus cereus*," The Journal of Antibiotics 41(2): 271-273 (1988).
Schiedlmeier et al., "Nuclearn Transformation of *Volvox carteri*," Proceedings of the National Academy of Sciences USA 91(11): 5080-5084 (May 1994).
Hallmann et al., "Genetic Engineering of the Multicellular Green Alga *Volvox*: A Modified and Multiplied Bacterial Antibiotic Resistance Gene as a Dominant Selectable Marker," The Plant Journal 17(1): 99-109 (Jan. 1999).
Minoda et al., "Improvement of Culture Conditions and Evidence for Nuclear Transformation by Homologous Recombination in a Red Alga, *Cyanidioschyzon merolae* 10D," Plant and Cell Physiology, vol. 45, No. 6, Jun. 2004, pp. 667-671.
Hallmann et al., "Gene Replacement by Homologous Recombination in the Multicellular Green Alga, *Volvox carteri*," Proceedings of the National Academy of Sciences in the United States of America, vol. 94, No. 14, 1997, pp. 7469-7474.

Kilian et al., "High-efficiency homologous recombination in the oil-producing alga *Nannochloropsis* sp.," Proceedings of the National Academy of Sciences of the United States of America, vol. 108, No. 52, Dec. 2001, pp. 21265-21269.
Extended European Search Report mailed Oct. 19, 2011 in European Patent Application 09759628.2, filed on Jun. 8, 2009.
Hallmann, "Algal Transgenics and Biotechnology," Transgenic Plant Journal, Global Science Books Ltd., GB, vol. 1, No. 1, Jan. 2007, pp. 81-98.
International Search Report and Written Opinion of the International Searching Authority mailed Oct. 20, 2010 for Application No. PCT/US2010/001754, filed Jun. 16, 2010.
International Search Report and Written Opinion of the International Searching Authority mailed Sep. 9, 2009 for Application No. PCT/US2009/046650, filed Jun. 8, 2009.
International Search Report and Written Opinion of the International Searching Authority mailed Jun. 15, 2011 for Application No. PCT/US2010/042666, filed Jul. 20, 2010.
Pollock, "High Carbon Dioxide Requiring Mutants of *Chlamydomonas reinhardtII*," Created Dec. 2003, [online, retrieved Oct. 14, 2010] <http://etd.Isu.edu/docs/available/etd-0828103-114026/unrestricted/Pollock_dis.pdf>.
Drocourt: GenBank Accession No: X52869.1, created Jan. 3, 1995.
Pan: GenBank Accession No: EE109892.1, created Jun. 23, 2008.
Pan: GenBank Accession No: EE109907, created Jun. 23, 2008.
Henriquez et al.: GenBank Accession No: Q07CY9, created Oct. 31, 2006.
International Search Report and Written Opinion of the International Searching Authority mailed Oct. 16, 2012 for Application No. PCT/US2012/035633, filed Apr. 27, 2012.
Yu et al., "Construction and characterization of a normalized cDNA library of *Nannochloropsis oculata* (Eustigmatophyceae)," Chinese Journal of Oceanology and Limnology, vol. 28, No. 4, pp. 802-807, 2010.
Lumbreras et al., "Efficient Foreign Gene Expression in *Chlamydomonas reinhardtii* Mediated by an Endogenous Intron," The Plant Journal, vol. 14, No. 4 Jan. 1, 1998, pp. 441-447, XP001150496, ISN: 0960-7412, DOI: 10.1046/j.1365-313X.1998.00145.X.
Rose A.B., "Intron-Mediated Regulation of Gene Expression," Current Topics in Microbiology and Immunology vol. 326, Jan. 1, 2008, pp. 277-290, XP009145370, ISSN: 0070-217X.
Rose A.B., "The Effect of Intron Location on Intron-Mediated Enhancement of Gene Expression in *Arabidopsis*," The Plant Journal, vol. 40, No. 5, Dec. 1, 2004, pp. 744-751, XP55029911, ISSN: 0960-7412, DOI:10.1111/j.1365-313X.2004.02247.
International Search Report and Written Opinion of the International Searching Authority mailed Sep. 13, 2013 in Application No. PCT/US2013/038939 filed Apr. 30, 2013.
Notice on the First Office Action mailed May 20, 2013 in Chinese Application No. 201080058106.7 filed Oct. 19, 2010.
Examination Report mailed Feb. 20, 2013 in Australian Application No. 2009274500 filed Jul. 24, 2009.
Examination Report mailed Apr. 29, 2013 in European Application No. 09759628.2 filed Jun. 8, 2009.
Examination Report mailed Aug. 29, 2013 in Australian Application No. 2009255947 filed Jun. 8, 2009.
Examination Report mailed Sep. 19, 2013 in Australian Application No. 2010310765 filed Oct. 19, 2010.
Notice on the Second Office Action mailed Sep. 24, 2013 in Chinese Application No. 200980138072.X filed Jul. 24, 2009.
Zuo-Xi Ruan et al., Effects of Acute Glyphosate Exposure on the Growth and Physiology of *Nostoc sphaeroides*, an Edible Cyanobacterium of Paddy Rice Fields, Acta Hydrobiologica Sinica, Jul. 2008 vol. 32, No. 4.
Santin-Montanya, I. "Optimal Growth of *Dunaliella primolecta* in Axenic Conditions to Assay Herbicides," Chemosphere, 66, Elsevier 2006, p. 1315-1322.
Felix, R. "Use of the cell wall-less alga *Dunaliella bioculata* in herbicide screening tests," Annals of Applied Biology, 113, 1988, pp. 55-60.

(56) References Cited

OTHER PUBLICATIONS

Janssen, M. "Phytosynthetic efficiency of *Dunaliella tertiolecta* under short light/dark cycles," Enzyme and Microbial Technology, 29, 2001, p. 298-305.

Saenz, M.E., "Effects of Technical Grade and a Commercial Formulation of Glyphosate on Algal Population Growth," Bulletin of Environmental Contamination Toxicology, 1997, 59: pp. 638-644.

Christy et al., "Effects of Glyphosate on Growth of Chlorella," Weed Science, vol. 29, Issue 1, Jan. 1981, pp. 5-7.

Roessler et al., "Genetic Engineering Approaches for Enhanced Production of Biodiesel Fuel from Microalgae," ACS Symposium Series; American Chemical Society, 1994, pp. 255-270.

Kureshy et al., "Effect of Ozone Treatment on Cultures of *Nannochloropsis oculata, Isochrysis galbana*, and *Chaetoceros gracilis*," Journal of the World Aquaculture Society, 1999, 30(4), pp. 473-480.

Genbank Accession No. U71602 (*Nannochloropsis* sp. Violaxanthing/chlorophyll a binding protein precursor (NANVCP) mRNA, 1996.

Sukenik et al. "Characterization of a Gene Encoding the Light-Harvesting Violaxanthin-Chlorophyll Protein of *Nannochloropsis* Sp. (Eustigmatophyceae)," Journal of Phycology, Jun. 2000; 36(3), pp. 563-570.

Abe et al., AG610981, *Musmusculus molossinus* DNA, 2004.

Kopczynski et al., CO268749, *Drosophila melanogaster* cDNA clone EK092604, 2004.

Csogor et al., "Light Distribution in a Novel Photobioreactor—Modelling for Optimization," Journal of Applied Phycology, vol. 13, pp. 325-333.

Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.

Zittelli et al., "Mass Cultivation of *Nannochloropsis* Sp. in Annular Reactors," Journal of Applied Phycology, vol. 15, pp. 107-113, Mar. 2003.

Strzepek et al., "Photosynthetic Architecture Differs in Coastal and Oceanic Diatoms," Nature, vol. 431, pp. 689-692, Oct. 2004.

Shi et al., "Analysis of Expressed Sequence Tags from the Marine Microalga *Nannochloropsis oculata* (eustigmatophyceae)," Journal of Phycol, vol. 44, pp. 99-102, 2008.

Thiel et al., "Transformation of a Filamentous Cyanobacterium by Electroporation," Journal of Bacteriology, Oct. 1989, vol. 171, No. 10, pp. 5743-5746.

Krienitz et al., "*Nannochloropsis limnetica* (Eustigmatophyceae), a new species of picoplankton from freshwater," Phycologia, 2000, vol. 39, No. 3, Abstract.

Lee et al., "Isolation and Characterization of a Xanthophyll Aberrant Mutant of the Green Alga *Nannochloropsis oculata*," Marine Biotechnology, 2006, vol. 8, pp. 238-245.

Sukenik et al., "Regulation of Fatty Acid Composition by Irradiance Level in the Eustigmatophyte *Nannochloropsis*," Journal of Phycol., 1989, vol. 25, pp. 686-692.

Rocha et al., "Growth Aspects of the Marine Microalga *Nannochlorpsis gaditana*," Biomolecular Engineering, 2003, vol. 20, pp. 237-242.

MacIntyre et al., "Primary Production by Suspended and Benthic Microalgae in a Turbid Estuary: Time-Scales of Variability in San Antonio Bay, Texas," Marine Ecology Progress Series, 1996, vol. 145, pp. 245-268.

Witkowski et al., "Conversion of a B-Ketoacyl Synthase to a Malonyl Decarboxylase by Replacement of the Active-Site Cysteine with Glutamine," Biochemistry, 1999, vol. 38, 11643-11650.

Kisselev, "Polypeptide Release Factors in Prokaryotes and Eukaryotes: Same Function, Different Structure," Structure, vol. 10, Jan. 2002.

Whisstock et al., "Predication of protein function from protein sequence and structure," Q. Rev. Biophysics, 2003, vol. 36, pp. 307-340.

Broun et al., "Catalytic Plasticity of Fatty Acid Modification Enzymes Underlying Chemical Diversity of Plant Lipids," Science, vol. 282, 1998.

Wishart et al., "A Single Mutation Converts a Novel Phosphotyrosine Binding Domain into a Dual-specificity Phosphatase," J. Biol. Chem. 1995, vol. 270(45), pp. 26782-26785.

Geng et al, "Construction of a System for the Stable Expression of Foreign Genes in *Dunaliella salina*," Acta Botanica Sinica 46(3): 342-346, 2004.

Chen et al., "Highly Efficient Expression of Rabbit Neutrophil Peptide-1 gene in Chlorella Ellipsoidea Cells," Current Genetics 39(5-6): 365-370, 2001.

Suga et al., "Control by Osmolarity and Electric Field Strength of Electro-Induced Gene Transfer and Protein Release in Fission Yeast Cells," Journal of Electrostatics 64(12): 796-801, 2006.

International Search Report mailed Sep. 16, 2009 for Application No. PCT/US2009/004296, filed Jul. 24, 2009.

Written Opinion of the International Searching Authority mailed Sep. 16, 2009 for Application No. PCT/US2009/004296, filed Jul. 24, 2009.

Office Action mailed Nov. 14, 2012 in China Patent Application No. 200980138072.X, filed Jul. 24, 2009.

Official Action mailed Jul. 10, 2012 in Mexico Patent Application No. MX/a/2011/000934, filed Jul. 24, 2009.

Official Action mailed Mar. 5, 2013 in Mexico Patent Application No. MX/a/2011/000934, filed Jul. 24, 2009.

Duarte et al., "Glyphosate (GP) Effects with Emphasis on Aquatic Organisms," Colunbia Orinoquia, ISSN: 0121-3709, pp. 70-100, 2004.

Technical Card: Glyphosate, Document filed for the Pesticide Action Network and the Alternatives Thereof, for Latin America (RAP-AL)-Communications and Administration Office, Apr. 2008.

Department of Environment, Housing and Territorial Development Ministry, Resolution (1009), published Jun. 17, 2008.

International Search Report and Written Opinion of the International Searching Authority mailed Oct. 30, 2009 for Application No. PCT/US2009/046656, filed Jun. 8, 2009.

International Search Report and Written Opinion of the International Searching Authority mailed Aug. 12, 2009 for Application No. PCT/US2009/003819, filed Jun. 25, 2009.

International Search Report and Written Opinion of the International Searching Authority mailed Dec. 20, 2010 for Application No. PCT/US2010/053265, filed Oct. 19, 2010.

Extended European Search Report mailed Mar. 19, 2013 in European Patent Application 10825551.4, filed on Oct. 19, 2010.

\* cited by examiner

FIG. 2

305 ───► <u>TGGTGGAGTTGACTATCGTGTGGA</u>

```
GTGTTTGGGGAGGGAAAGGGCGGAGCGTGAGTGCAATGCGAGGTGGGCGAAGTGGGCATGTGaTA
AATGGCTGTGTGGTGGAGGCCTTCGCTGCGTGTCTGTGACTGTCTTGATTGTGTGCTTAGAGTGAGA
TACCAAAGCAAGATCTTCCCTGCCATCCCTTCATTGTCCCACGGGCCGAAGAgATGGGGGCTTGACG
AGAGGACAGGGATGCAGGTGCGATGCGGTCCTGTCCATGGGGCAGGAACCGCTGGGGTGCAGTGG
CACAGAAGACAGAAGGaGAAAACACATGCACCAAATAAACATATGACAAAGAGTCAAGCAGTAGTC
AAAACAACCAAAACGTAAGCAAGACGGAACAAGATGGCACGCGTCTGCAACAGACCGGCTCGCGCC
GAACGTGCCTCCTGCTTTTCAACGATCCTGCGAGGTCAACCAGGATTTGCTCGCCGGGACGATTTCAT
CCCCTTATCAACGAGCCCTTGAGGCTCCAGGCGTGCTTCCACACCCCAGTTGGTAACAGGACATTGG
GGCATCTTGCCTATCTTGTCTTAGTGCCGAAAGCCTCAACGACCTCCCATGGGGTCTGCTCAACGCCT
CAACCTTGCAGTAAGGATCCCCGAGGGCAAGACCCGCAAAGCCTTCTGTCGTCGGACAAAGCGGAG
CGAGGGAACAGGCTCAGCTCAACCCTCTTGAGAGCCCATAAGTGCCCCCTGATCTATCTTCAACAGTC
TTTCCCTGTCACAAGAAAACCCAGCTAGTTGACCAAGTTGCTAGAGCTGATACCTTGTACTTCGCTCTT
TGTGTGCTTTACCTGATTGGACATGGACAGACCTCCCCTTGCTCTTCCTTCTAGGAGCCTGGGCTCTCG
CTCCTTGTCTTTCGAGAGACCTTTCCCTTGAGTTGCGTATCCAGCGATCAAGTATGAAGAGTGCTTTCA
AACCTAGATACGTTCTGCCCAGTTCTCTTGCCCTTTTCCACACGTGCTCCACATCTTCACACGACTCGC
ACCATACCCGACGAAACCCCTCAAAACATCGCAACACTTACATCCGCTCGTGTCCCACCCCCGATGC
CATATCCTCTACAGCAGCAGCACCACCACCACCACTTCTTAAGT
``` } 310

315 ───► <u>ATGGCCAAGTTGACCAGTGCCGTTCCGGTGCTCACCGCGCGCGACGTCGCCGGAGCGGTCGAGTTC</u>
```
TGGACCGACCGGCTCGGGTTCTCCCGGGACTTCGTGGAGGACGACTTCGCCGGTGTGGTCCGGGAC
GACGTGACCCTGTTCATCAGCGCGGTCCAGGACCAGGTGGTGCCGGACAACACCCTGGCCTGGGTG
TGGGTGCGCGGCCTGGACGAGCTGTACGCCGAGTGGTCGGAGGTCGTGTCCACGAACTTCCGGGA
CGCCTCCGGGCCGGCCATGACCGAGATCGGCGAGCAGCCGTGGGGGCGGGAGTTCGCCCTGCGCG
ACCCGGCCGGCAACTGCGTGCACTTCGTGGCCGAGGAGCAGGACTAA
``` ◄─── 320

```
GCTTCTGTGGAAGAGCCAGTGGTAGTAGCAGTAGCAGCAGCAGTAGCAGCCGCAGCACTCAGTGT
TGGCGCGAGAGATTGTCCATCCCTTCTTAACCTACCGGAAGAGAAATAAGGCCTTTCTCCCGTAGCT
GTCTTCGTTTGTTTGTGCTGATTGCTTGATATGAGAGTGTTGAATTCCTGCATCATGTTTTTCTCTGTA
GTCCTTTCCTACCCCCGTCATTTTCTTTTCTCCCTGGTTCTTCTTTTGTCACCCTTATTTTACATAAAATT
TTCTTTGTTTATAGTGAGAGGAAGGTAGAGAGGGGAAAACAAGAACAACGAACGCAAGCGTGTG
AAAGGAGGGCGAGTAGAAGAGAAACAGATCTGTTGAGCATTGAGAGTGGAGCCGGGGGAAAGG
CTTGTGTGTTGTCTTTGAAAAAGTTGTTTAAATCACGAATCCGTTAGTTCTCATGTGTACCTCTTTCA
CTACATGTGATGGAGAAAACAAAAGTGTGAGGATTAATTGAAGAAAAAAGAAGAGTTCGACACGT
CAAACCGCCCAAAAGACGTCACAAAGAGAACTTGATTCTCTTTGCCGTGTTGATCCTGTCTTTTCCCCC
AGCTTTTCTTGCCACCCGT<u>GGCACACGAGATGGACAAGATCAG</u>
``` } 325

GENES FOR ENHANCED LIPID METABOLISM FOR ACCUMULATION OF LIPIDS

CROSS-REFERENCE TO RELATED APPLICATIONS

The present application is related to U.S. Non-Provisional patent application Ser. No. 12/706,683 filed on Feb. 16, 2010, titled "Bidirectional Promoters in *Nannochloropsis*," which is hereby incorporated by reference.

The present application is related to U.S. Non-Provisional patent application Ser. No. 12/581,812 filed on Oct. 19, 2009, titled "Homologous Recombination in an Algal Nuclear Genome," which is hereby incorporated by reference.

The present application is related to U.S. Non-Provisional patent application Ser. No. 12/480,635 filed on Jun. 8, 2009, titled "VCP-Based Vectors for Algal Cell Transformation," which is hereby incorporated by reference.

The present application is related to U.S. Non-Provisional patent application Ser. No. 12/480,611 filed on Jun. 8, 2009, titled "Transformation of Algal Cells," which is hereby incorporated by reference.

BACKGROUND OF THE INVENTION

Field of the Invention

This invention relates to molecular biology, and more specifically to the enhanced expression of metabolic genes associated with lipid metabolism.

REFERENCE TO SEQUENCE LISTINGS

The present application is filed with sequence listing(s) attached hereto and incorporated by reference.

BRIEF SUMMARY OF THE CLAIMED INVENTION

Provided herein are exemplary genes, constructs and methods for the formation of triacylglycerols (TAGs). The exemplary genes include a phosphatic acid phosphohydrolase (PA Hydrolase) gene, a diacylglycerol o-acyltransferase (DAGAT2A) gene, and a phospholipid:diacylglycerol acyltransferase (LROI) gene.

BRIEF DESCRIPTION OF THE FIGURES AND SEQUENCES

FIG. 2 shows an exemplary gene sequence of the genome in *Nannochloropsis*, which includes the LROI gene.

Figure 1:
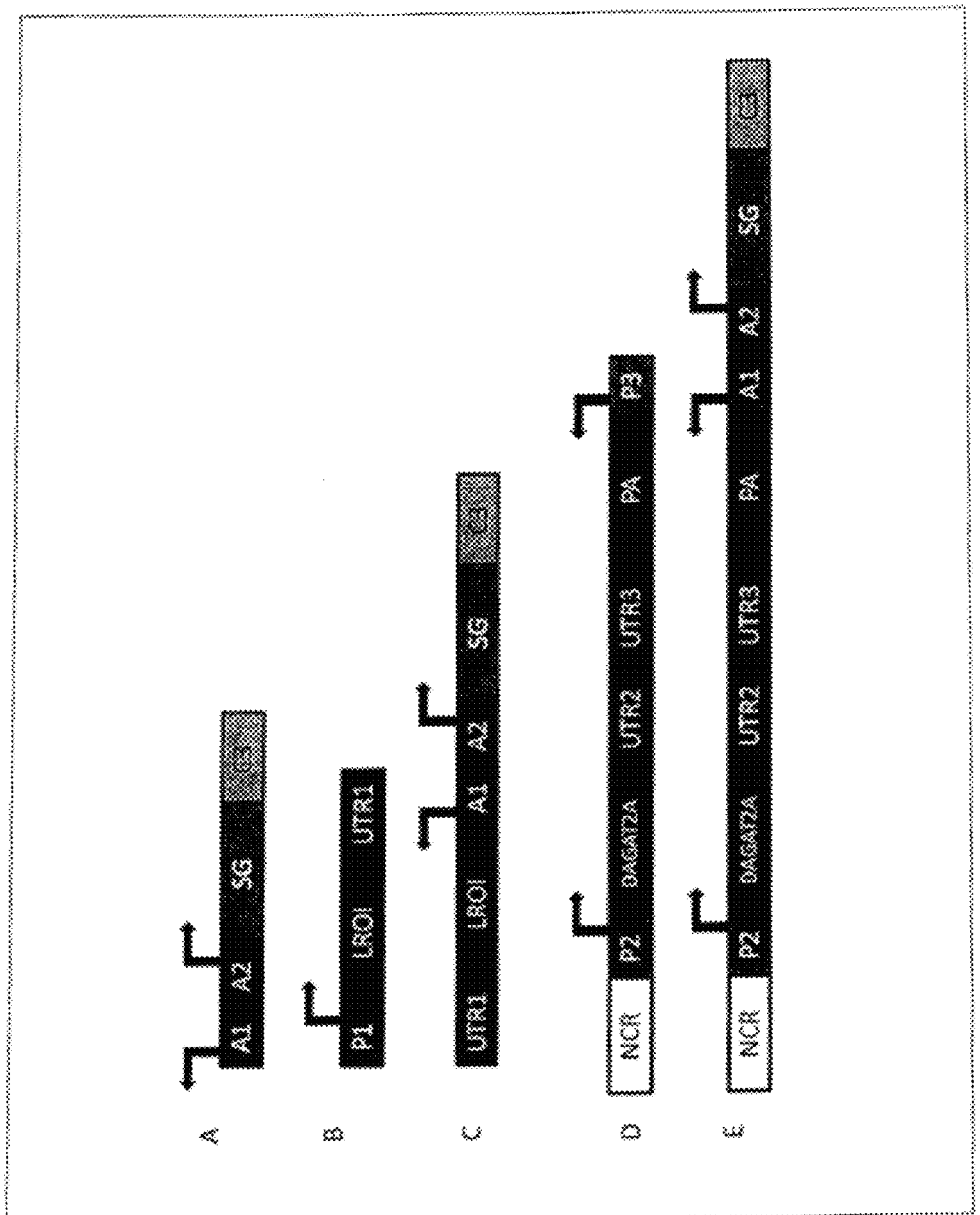
FIG. 1 shows a schematic representation of exemplary constructs, according to various exemplary embodiments.

FIG. 3 shows an exemplary gene sequence of a transformation construct, which includes a bidirectional promoter, as described in U.S. patent application Ser. No. 12/706,683 titled "Bidirectional Promoters in *Nannochloropsis*," as filed on Feb. 16, 2010. The exemplary transformation construct includes a marker gene, such as the sh ble gene, and an untranslated region as a regulatory element, as also described in U.S. patent application Ser. No. 12/706,683.

Figure 4:
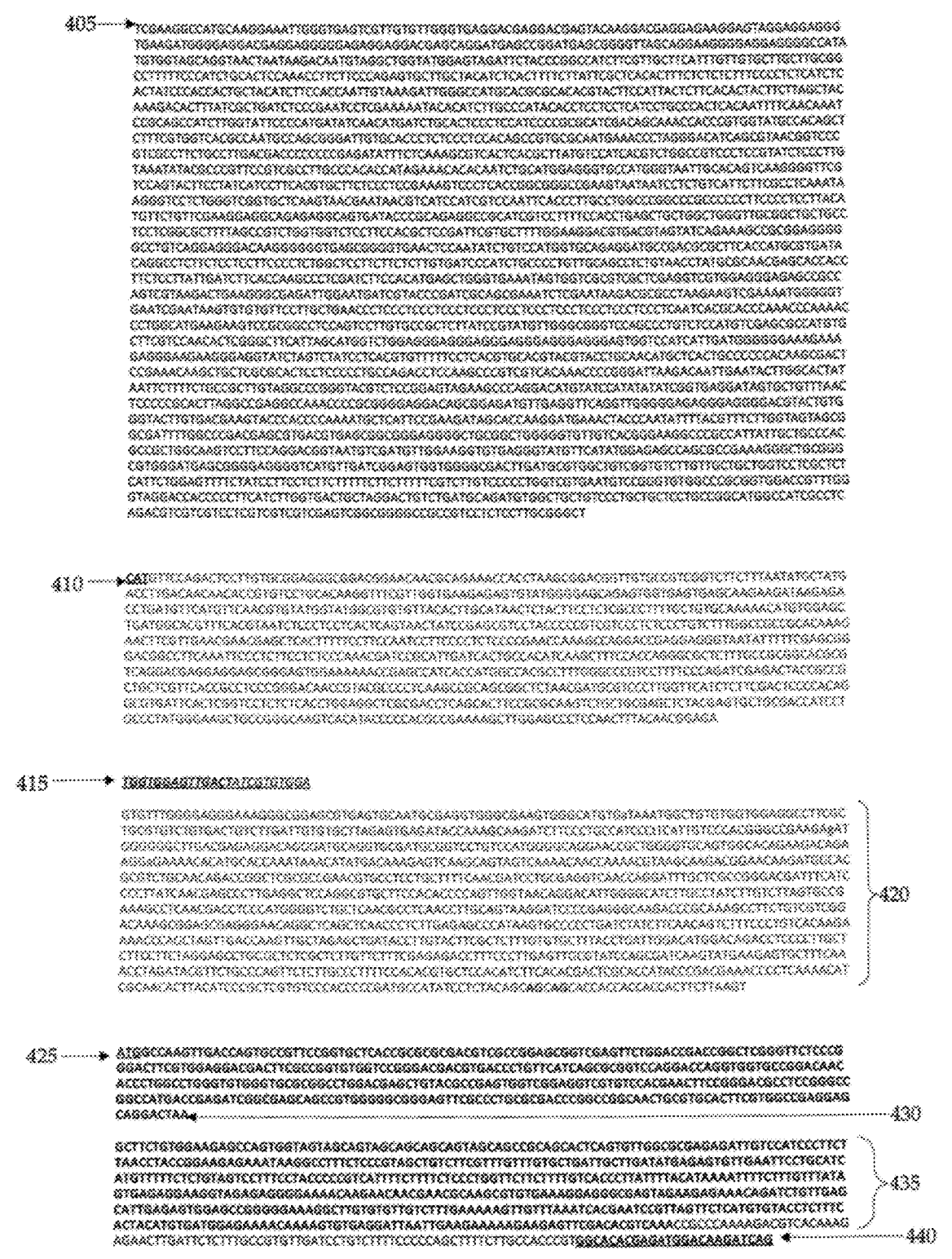

FIG. 4 shows an exemplary gene sequence of a transformation construct that includes a gene of interest, such as the LROI gene and a selection marker.

Figure 5:
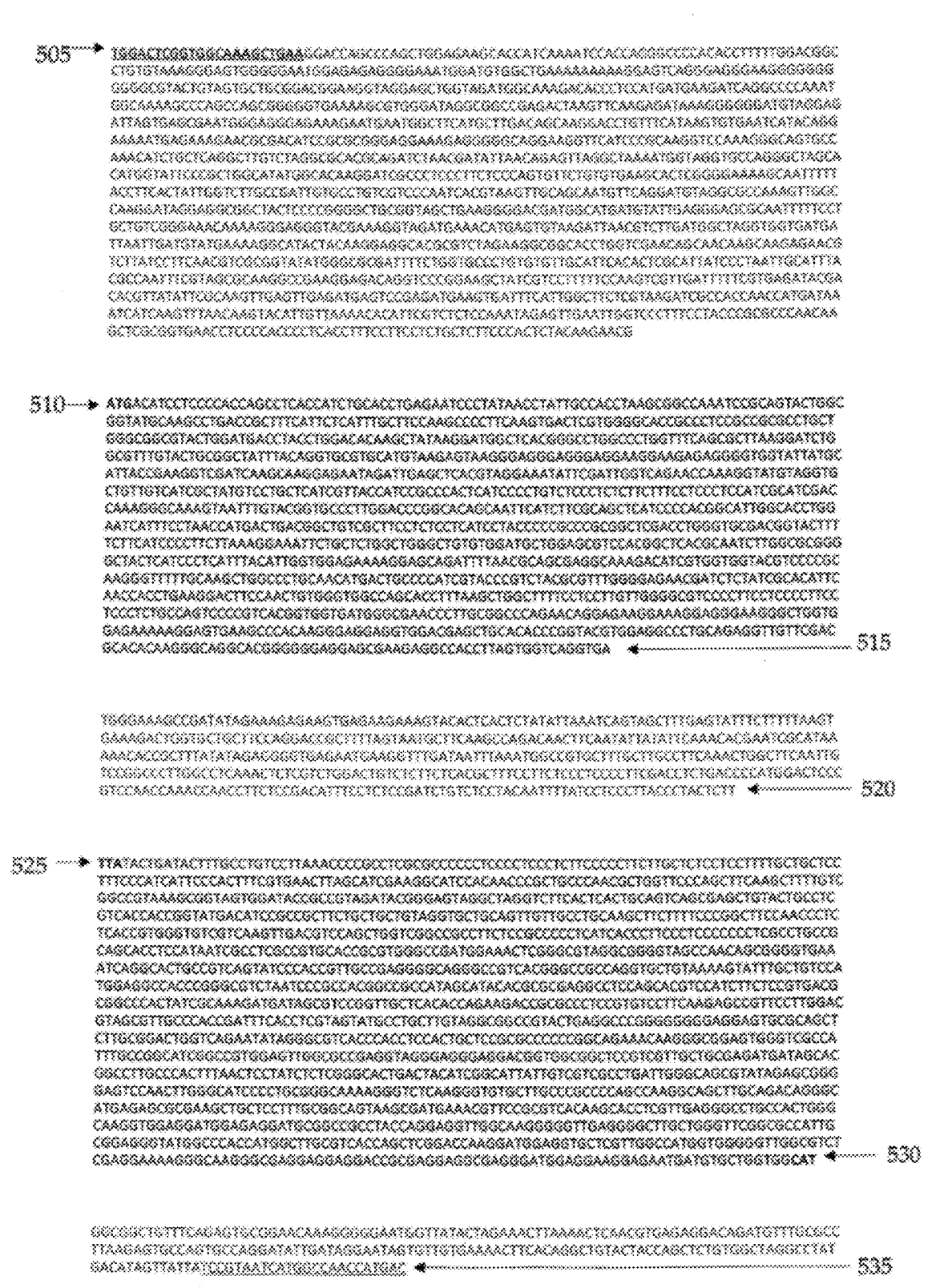

FIG. 5 shows an exemplary gene sequence of genomic DNA that includes a phosphatic acid phosphohydrolase (PA Hydrolase) gene and a diacylglycerol o-acyltransferase (DAGAT2A) gene used to design an exemplary F299 transformation construct gene sequence.

Figure 6:
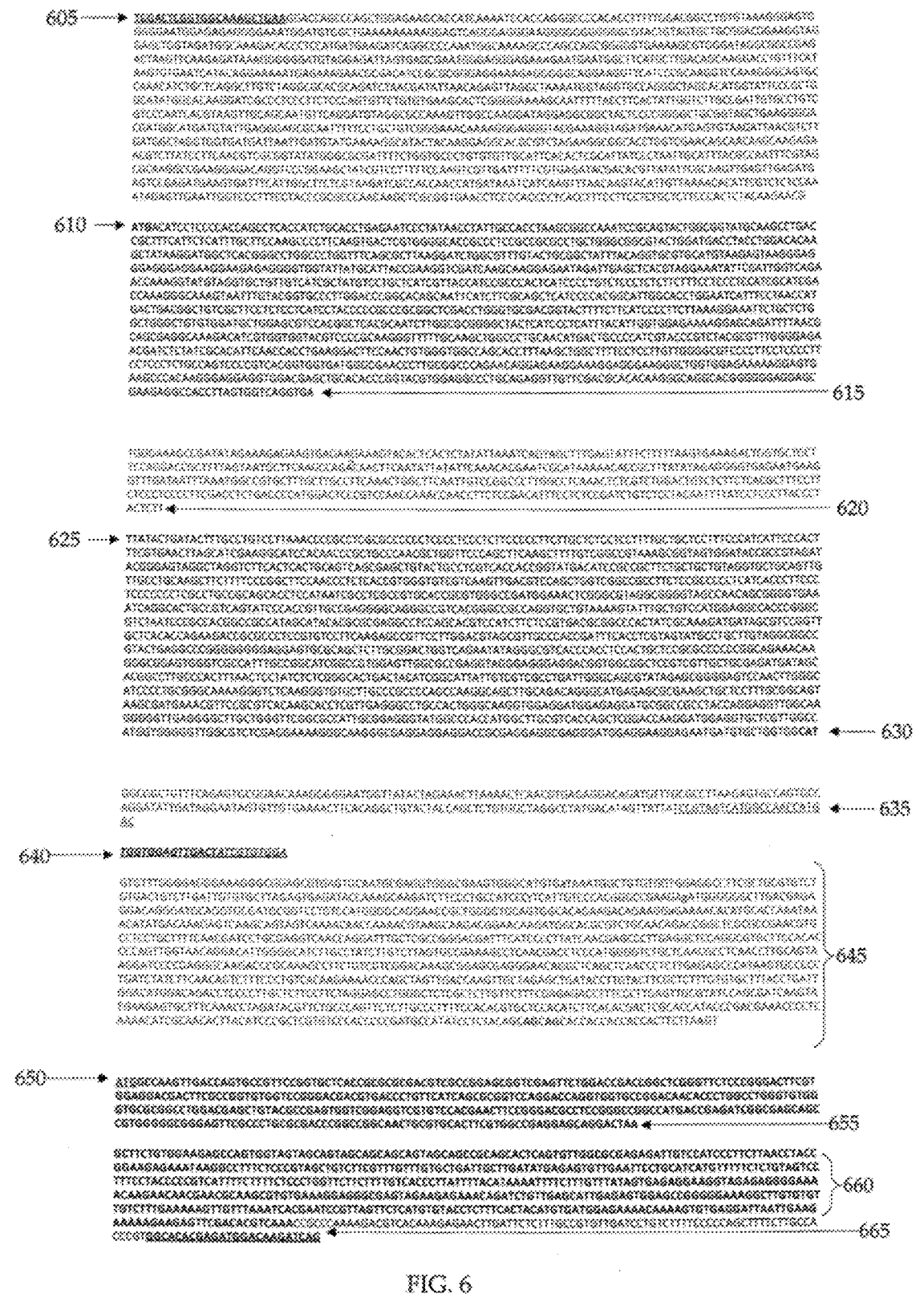

FIG. 6 shows an exemplary F299 transformation construct gene sequence.

SEQ. ID NO. 1 shows an exemplary nucleotide sequence for a phospholipid:diacylglycerol acyltransferase (LROI) gene.

SEQ. ID. NO. 2 shows an exemplary nucleotide sequence for a diacylglycerol o-acyltransferase (DAGAT2A) gene.

SEQ. ID. NO. 3 shows an exemplary nucleotide sequence for a phosphatic acid phosphohydrolase (PA Hydrolase) gene.

SEQ. ID NO. 4 shows an exemplary partial amino acid sequence for the amino acid produced by the exemplary phospholipid:diacylglycerol acyltransferase (LROI) gene of SEQ. ID. NO. 1.

SEQ. ID. NO. 5 shows an exemplary partial amino acid sequence for the amino acid produced by the exemplary diacylglycerol o-acyltransferase (DAGAT2A) gene of SEQ ID. NO. 2.

SEQ. ID. NO. 6 shows an exemplary amino acid sequence for the amino acid produced by the exemplary phosphatic acid phosphohydrolase (PA Hydrolase) gene of SEQ. ID. No. 3.

SEQ. ID. NO. 7 shows the artificial sequence, "Synthetic EP259 Primer, " which is used to amplify the genomic DNA.

SEQ. ID. NO. 8 shows the artificial sequence, "Synthetic P260 Primer, " which is used to amplify the genomic DNA.

SEQ. ID. NO. 9 shows the artificial sequence, "Synthetic P119 Primer, " which is used to amplify the genomic DNA.

SEQ. ID. NO. 10 shows the artificial sequence, "Synthetic EP298 Primer, " which is used to amplify the genomic DNA.

SEQ. ID. NO. 11 shows the artificial sequence, "Synthetic P299 Primer, " which is used to amplify the genomic DNA.

SEQ. ID. NO. 12 shows the artificial sequence, "Synthetic P119 Primer, " which is used to amplify the genomic DNA.

DETAILED DESCRIPTION OF THE INVENTION

Provided herein are exemplary genes, constructs and methods for the formation of triacylglycerols (TAGs). The exemplary genes include a phosphatic acid phosphohydrolase (PA Hydrolase) gene, a diacylglycerol o-acyltransferase (DAGAT2A) gene, and a phospholipid:diacylglycerol acyltransferase (LROI) gene.

FIG. 1 shows a schematic representation of exemplary constructs, according to various exemplary embodiments.

Schematic A shows a bidirectional promoter construct, as described in U.S. patent application Ser. No. 12/706,683 titled "Bidirectional Promoters in *Nannochloropsis*," as filed on Feb. 16, 2010. The bidirectional promoter A1A2 drives expression of the selection gene (SG) at A2. C3 is the untranslated (UTR) region used in the construct.

Schematic B shows a LROI gene encoding a phospholipid:diacylglycerol acyltransferase, as found in the genome of *Nannochloropsis*. The LROI gene is transcribed by its promoter (P1), and followed by its own 3'untranslated region (UTR1).

Schematic C shows the LROI transformation construct (F260). The LROI gene and its own UTR1 were fused to the transformation construct as depicted in Schematic A in a way that LROI expression would be driven by the A1 part of the bidirectional promoter.

Schematic D shows the structure of the gene cluster around DAGAT2A and PA. Each of the genes is preceded by a promoter (i.e. DAGAT2A by promoter P2, PA by promoter P3).

Each gene is followed by its own UTR (DAGAT2A by UTR2 and PA by UTR3). A non-coding region (NCR) is indicated in front of the promoter.

Schematic E shows the construct derived by fusion of the DAGAT2A-PA cluster from Schematic D with the bidirectional promoter construct from Schematic A.

The genomic cluster shown in Schematic D is fused to the transformation construct shown in Schematic A, so that the PA gene is driven by the bidirectional promoter A1. For this purpose, the native promoter P3 is replaced by the construct shown in Schematic A. Note that the NCR has been retained in order to allow space for random recombination into the genome without impairing function of the promoter P2. The entire construct is designated F299.

In F299, the phosphate group of phosphatic acid (diacylglycerol phosphate) is cleaved off by the enzyme PA hydrolase resulting in diacyl-glycerol and phosphate. Notably, diacyl-glycerol is believed to be activated for further TAG synthesis. In the next step towards the synthesis of TAGs, a third fatty acid is attached by the enzyme diacylglycerol-o-acyltransferase (DAGAT), thus yielding TAG. The inventors identified several PA hydrolases and several type 2 DAGAT genes (designated DAGAT2A, DAGAT2B, DAGAT2C) in the genome of *Nannochloropsis*. Interestingly, one copy of these genes, DAGAT2A, is located in a genomic cluster with a PA gene as indicated in Schematic D. The inventors made a construct as illustrated in Schematic E, (i.e., the PA hydrolase gene under control of the bidirectional promoter of Schematic A and the DAGAT2A gene under control of its own promoter, as indicated in Schematic D). The inventors designated the transformation construct illustrated in Schematic E as F299.

In F260, the gene LRO1 encodes a phospholipid:diacylglycerol acyltransferase. Its function is the catalysis of the following reaction:

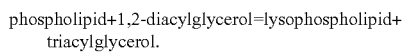

phospholipid+1,2-diacylglycerol=lysophospholipid+ triacylglycerol.

Thus, fatty acyl groups from phospholipids are transferred to diacylglycerol in order to form TAGs. The inventors fused the gene encoding the *Nannochloropsis* LRO1 gene (illustrated in schematic B) to the bidirectional promoter construct (Schematic A) in order to form the final expression construct F260 (illustrated in Schematic C). The promoter or LRO1 is thus replaced by the A1 part of the bidirectional promoter.

Figure 2:
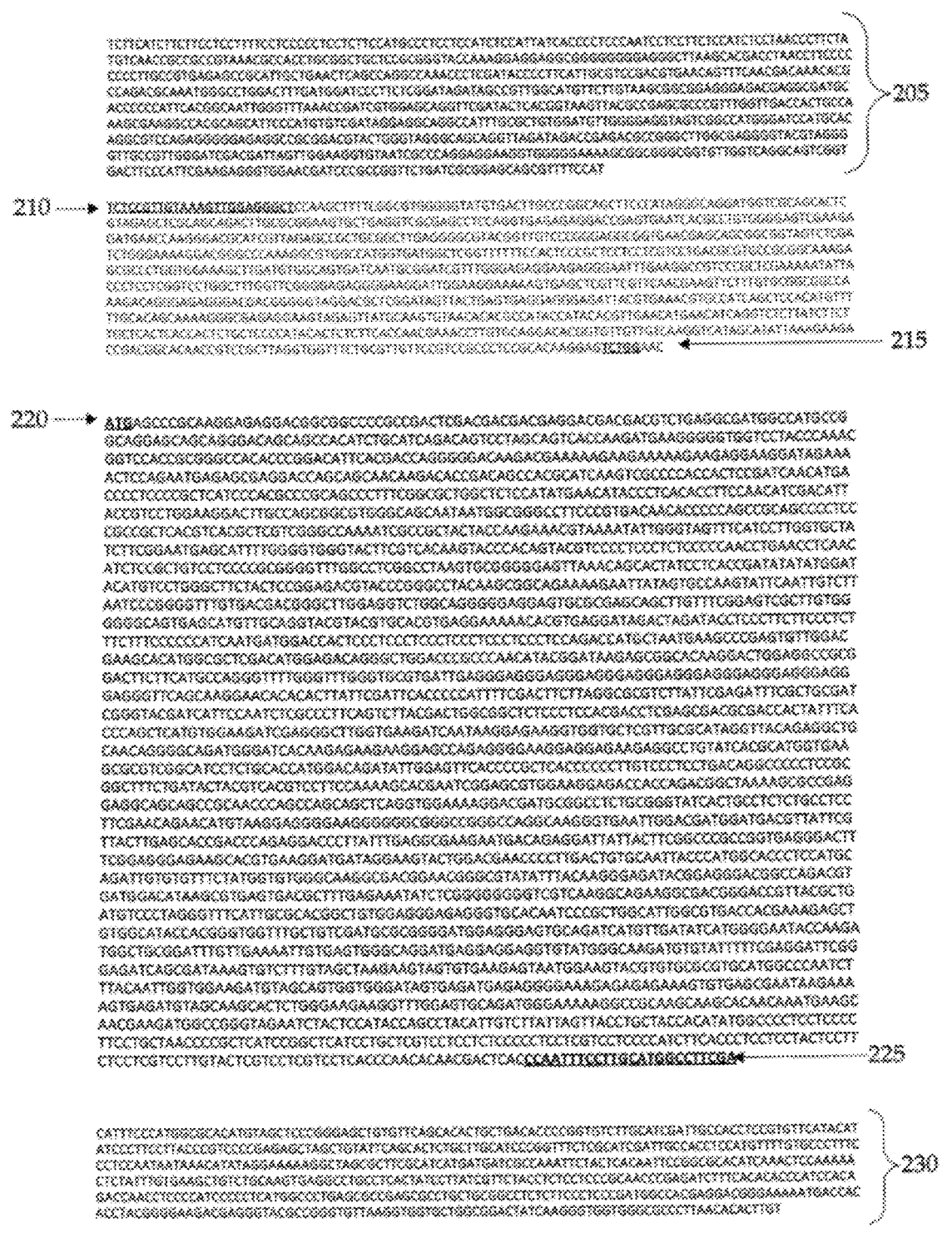

FIG. 2 shows an exemplary gene sequence of the genome in *Nannochloropsis*, which includes the LRO1 gene. 205 shows a first portion of continuous genomic DNA outside of the gene sequence of interest. 210 shows part of the EP259 primer sequence used to amplify the gene. 215 shows the putative transcription start. 220 shows the putative methionine codon (reading frame left to right). 225 shows the P260 sequence. 230 shows a second portion of continuous genomic DNA outside of the gene sequence of interest.

FIG. 3 shows an exemplary gene sequence of a transformation construct, which includes a bidirectional promoter, as described in U.S. patent application Ser. No. 12/706,683 titled "Bidirectional Promoters in *Nannochloropsis*," as filed on Feb. 16, 2010. The exemplary transformation construct includes a marker gene, such as the sh ble gene, and an untranslated region as a regulatory element, as also described in U.S. patent application Ser. No. 12/706,683. 305 shows the site for the primer for amplification of the transformation construct. This is the target for the fusion primer EP259. 310 shows a close sequence homology to that of the bidirectional promoter (A1A2 in FIG. 1) of the VCP2 gene. 315 shows the start codon for the sh ble gene. 320 shows the stop codon for the sh ble gene. 325 shows a 3' UTR of the VCP1. 330 shows the P119 primer sequence.

FIG. 4 shows an exemplary gene sequence of a transformation construct including a gene of interest, such as the LRO1 gene and a selection marker. 405 to and including 410 shows the reverse complement of the sequence depicted in FIG. 2 (220 to 225). The first 3 BP in 410 show the methionine codon (reading frame right to left).

The sequence beginning at 415 shows the bidirectional promoter construct, this sequence 415 (the few nucleotides) being part of the primer used to amplify the LRO1 gene cluster in order to achieve a fusion with the bidirectional promoter via PCR. 420 shows a close sequence homology to that of the bidirectional promoter (A1A2 in FIG. 1). 425 shows the start codon for the sh ble gene. 430 shows the stop codon for the sh ble gene. 435 shows a 3' UTR of the VCP1. 440 shows the P119 primer sequence.

FIG. 5 shows an exemplary gene sequence of genomic DNA that includes a phosphatic acid phosphohydrolase (PA Hydrolase) gene and a diacylglycerol o-acyltransferase (DAGAT2A) gene used to design an exemplary F299 transformation construct gene sequence. 505 shows where P299 binds. 510 shows the putative start methionine of the gene DAGAT2A. 505 through 510 represents a promoter region. 515 shows the putative stop codon of DAGAT2A. 515 through 520 represents the overlapping 3' UTR regions of the genes DAGAT2A and PA hydrolase. 525 shows the stop codon of the PA hydrolase gene. 530 shows the start codon of the PA hydrolase gene. 535 shows where EP298 binds (EP298 is a fusion primer and also contains elements of the bidirectional promoter).

FIG. 6 shows an exemplary F299 transformation construct gene sequence. 605 shows where P299 binds. 610 shows the putative start methionine of the DAGAT2A gene. 605 through 610 represents a promoter region. 615 shows the putative stop codon of DAGAT2A. 610 shows the putative start methionine of the gene DAGAT2A. 615 through 620 represents the overlapping 3' UTR overlapping regions of the genes DAGAT2A and PA hydrolase. 625 shows the stop codon of the PA hydrolase gene. 630 shows the start codon of the PA hydrolase gene. 640 shows part of the bidirectional promoter construct, this sequence is part of the primer. EP298 which binds to both 635 and 640 (EP298 is a fusion primer and also contains elements of the bidirectional promoter). 645 shows a close sequence homology to that of the bidirectional promoter (A1A2 in FIG. 1) of the VCP2 gene. 650 shows the start codon for the sh ble gene. 655 shows the stop codon for the sh ble gene. 660 shows a 3' UTR of the VCP1. 665 shows the P119 primer sequence.

EXAMPLE ONE

The inventors used the constructs F260 and F299 for transformation experiments in *Nannochloropsis* and obtained transformants growing on the selection agent. Both linear constructs (F299 and F260) have ends derived from different locations of the *Nannochloropsis* genome (i.e. they are not in proximity in the target genome), thus the constructs are believed to mostly integrate randomly into the genome of *Nannochloropsis*.

The inventors subsequently screened transformants for enhanced properties in regard to lipid accumulation. Lipid accumulation was followed via nile red staining and subsequent analysis in a flow cytometer.

Cells were grown in log phase in medium which allows for growth to a density of ~24.000 cells/µl before growth ceases (because of a Nitrogen limitation). At the onset of Nitrogen starvation, lipid accumulation starts. Samples were collected every day and frozen. Later, all samples were nile red stained and analyzed in a Accuri cytometer for oil content per cell. On average, 50,000 cells per sample were analyzed and nile red fluorescence averaged. The mean of relative nile red fluorescence provided insight into the oil content per cell, wt cells were grown and starved the same way and served as a control. Out of this screen the inventors identified a few transformants that have enhanced oil accumulation profiles, when compared to the wildtype. The inventors concluded that the expression of the constructs F299 and/or F260 allows an increase of lipid accumulation or accelerates lipid accumulation.

Primers Used to Amplify the Genomic DNA.

EP259: TCCACACGATAGTCAACTCCACCA

TCTCCGTTGTAAAGTTGGAGGGCT:

Note that the 1st part is homologous to the bidirectional promoter construct and is used for the fusion PCR (LRO1 to bidirectional promoter).

P260: TCGAAGGCCATGCAAGGAAATTGG:

This primer is located at the end of the gene (after 3'UTR).

P119: CTGATCTTGTCCATCTCGTGTGCC:

This is the primer sitting on the very end of the bidirectional promoter construct.

The genomic DNA cluster was amplified with P260 and EP259 and the obtained fragment purified. A fusion PCR was performed with this fragment and a bidirectional promoter construct (as indicated herein) employing the primers P119 and P260.

The resulting construct (~6.3 kB) was named F260 and used directly for transformation in *Nannochloropsis* and selected on zeocine.

EP298 TCCACACGATAGTCAACTCCACCA

GTCATGGTTGGCCATGATTACGGA:

This primer contains the fusion site for the bidirectional promoter construct. It binds in front of the promoter structure of the PA hydrolase.

P299 ATGGACTCGGTGGCAAAGCTGAA:

This primer binds in front of the promoter structure of the DAGAT2A gene.

The genomic DNA cluster was amplified with P299 and EP298 and the obtained fragment purified. A fusion PCR was performed with this fragment and a bidirectional promoter construct (as indicated herein) employing the primers P119 and P299.

The resulting construct (~7.0 kB) was named F299 and used directly for transformation in *Nannochloropsis* and selected on zeocine.

P119: CTGATCTTGTCCATCTCGTGTGCC:

This is the primer sitting on the very end of the bidirectional promoter construct.

While various embodiments are described herein, it should be understood that they are presented by way of example only, and not limitation. Thus, the breadth and scope of a preferred embodiment should not be limited by any of the described exemplary embodiments.

What is claimed is:

1. A method for increasing lipid accumulation compared to a wild-type algal cell, the method comprising transforming an algal cell with the nucleotide sequence set forth in SEQ. ID. NO. 1.

2. The method of claim 1, wherein a promoter in an expression vector increases expression of the nucleotide sequence compared to a wild-type algal cell.

3. The method of claim 1, wherein the algal cell is of algal genus *Nannochloropsis*.

4. A method for increasing lipid accumulation compared to a wild-type algal cell, the method comprising transforming an algal cell with the nucleotide sequence set forth in SEQ. ID. NO. 2.

5. The method of claim 4, wherein a promoter in an expression vector increases expression of the nucleotide sequence compared to a wild-type algal cell.

6. The method of claim 4, wherein the algal cell is of algal genus *Nannochloropsis*.

7. A method for increasing lipid accumulation compared to a wild-type algal cell, the method comprising transforming an algal cell with the nucleotide sequence set forth in SEQ. ID. NO. 3.

8. The method of claim 7, wherein a promoter in an expression vector increases expression of the nucleotide sequence compared to a wild-type algal cell.

9. The method of claim 7, wherein the algal cell is of algal genus *Nannochloropsis*.

10. A method for increasing lipid accumulation compared to a wild-type algal cell, the method comprising transforming an algal cell with the nucleotide sequences set forth in SEQ. ID. NO. 1 and SEQ. ID. NO. 2.

11. A method for increasing lipid accumulation compared to a wild-type algal cell, the method comprising transforming an algal cell with the nucleotide sequences set forth in SEQ. ID. NO. 1 and SEQ. ID. NO. 3.

12. A method for increasing lipid accumulation compared to a wild-type algal cell, the method comprising transforming an algal cell with the nucleotide sequences set forth in SEQ. ID. NO. 2 and SEQ. ID. NO. 3.

13. A method for increasing lipid accumulation compared to a wild-type algal cell, the method comprising transforming an algal cell with the nucleotide sequences set forth in SEQ. ID. NO. 1, SEQ. ID. NO. 2, and SEQ. ID. NO. 3.

* * * * *

SEQUENCE LISTING

```
<160> NUMBER OF SEQ ID NOS: 12

<210> SEQ ID NO 1
<211> LENGTH: 2994
<212> TYPE: DNA
<213> ORGANISM: Nannochloropsis

<400> SEQUENCE: 1
atgagcccgc aaggagagga cggcggcccc gccgactcga cgacgacgag gacgacgacg      60
tctgaggcga tggccatgcc ggcaggagca gcaggggacag cagccacatc tgcatcagac     120
agtcctagca gtcaccaaga tgaaggggggt ggtcctaccc aaacggtcca ccgcgggcca    180
cacccggaca ttcacgacca ggggggacaag acgaaaaaga agaaaaagaa gaggaaggat    240
agaaaactcc agaatgagag cgaggaccag cagcaacaag acaccgacag ccacgcatca    300
agtcgcccca ccactccgat caacatgacc cctccccgct catcccacgc ccgcagccct   360
ttcggcgctg gtctccata tgaacatacc ctcacaccctt ccaacatcga cattaccgtc    420
ctggaaggac ttgccagcgg cgtgggcagc aataatggcg ggccttcccg tgacaacacc    480
cccagccgca gcccctcccg ccgctcacgt cacgctcgtc gggccaaaat cgccgctact    540
accaagaaac gtaaaatatt gggtagtttc atccttggtg ctatcttcgg aatgagcatt    600
ttggggtggg tacttcgtca caagtaccca cagtacgtcc cctccctctc ccccaacctg    660
aacctcaaca tctccgctgt cctccccgcg gggtttggcc tcggcctaag tgcgggggag   720
```

```
ttaaacagca ctatcctcac cgatatatat ggatacatgt cctgggcttc tactccggag    780
acgtacccgg gcctacaagc ggcagaaaag aattatagtg ccaagtattc aattgtctta    840
atcccggggt ttgtgacgac gggcttggag gtctggcagg gggaggagtg cgcgagcagc    900
ttgtttcgga gtcgcttgtg gggggcagtg agcatgttgc aggtacgtac gtgcacgtga    960
ggaaaaacac gtgaggatag actagatacc tccttcttc cctctttctt tcccccatc    1020
aatgatggac cactccctcc ctccctccct ccctccctcc agaccatgct aatgaagccc   1080
gagtgttgga cgaagcacat ggcgctcgac atggagacag ggctggaccc gcccaacata   1140
cggataagag cggcacaagg actggaggcc gcggacttct tcatgccagg gttttgggtt   1200
tgggtgcgtg attgagggag ggagggaggg agggagggag ggagggaggg agggagggtt   1260
cagcaaggaa cacacactta ttcgattcac ccccattttc gacttcttag gcgcgtctta   1320
ttcgagattt cgctgcgatc gggtacgatc attccaatct cgcccttcag tcttacgact   1380
ggcggctctc cctccacgac ctcgagcgac gcgaccacta tttcacccag ctcatgtgga   1440
agatcgaggg cttggtgaag atcaataagg agaaggtggt gctcgttgcg cataggttac   1500
agaggctgca acaggggcag atgggatcac aagagaagaa ggagccagag gggaaggagg   1560
agaagaggcc tgtatcacgc atggtgaagc gcgtcggcat cctctgcacc atggacagat   1620
attggagttc accccgctca ccccccttgt ccctcctgac aggccccctc cgcggctttc   1680
tgatactacg tcacgtcctt ccaaaagcac gaatcggagc gtggaaggag accaccagac   1740
ggctaaaagc gccgaggagg cagcagccgc aacccagcca gcagctcagg tggaaaagga   1800
cgatgcggcc tctgcgggta tcactgcctc tctgcctcct tcgaacagaa catgtaagga   1860
ggggaagggg ggcgggccgg gccaggcaag ggtgaattgg acgatggatg acgttattcg   1920
ttacttgagc accgacccag aggacccta tttgaggcga agaatgacag aggattatta   1980
cttcggcccg ccggtgaggg actttcggag ggagaagcac gtgaaggatg ataggaagta   2040
ctggacgaac cccttgactg tgcaattacc catggcaccc tccatgcaga ttgtgtgttt   2100
ctatggtgtg ggcaaggcga cggaacgggc gtatatttac aagggagata cggagggacg   2160
gccagacgtg atggacataa gcgtgagtga cgctttgaga aatatctcgg gggggtcgt   2220
caaggcagaa ggcgacggga ccgttacgct gatgtcccta gggtttcatt gcgcacggct   2280
gtggagggag agggtgcaca atcccgctgg cattggcgtg accacgaaag agctgtggca   2340
taccacgggt ggtttgctgt cgatgcgcgg ggatggaggg agtgcagatc atgttgatat   2400
catggggaat accaagatgg ctgcggattt gttgaaaatt gtgagtgggc aggatgagga   2460
ggaggtgtat gggcaagatg tgtattttc gaggattcgg gagatcagcg ataaagtgtc   2520
tttgtagcta agaagtagtg tgaagagtaa tggaagtacg tgtgcgcgtg catggcccaa   2580
tctttacaat tggtggaaga tgtagcagtg gtgggatagt gagatgagag ggggaaagaga   2640
gagaaagtgt gagcgaataa gaaaagtgag atgtagcaag cactctggga agaaggtttg   2700
gagtgcagat gggaaaaagg ccgcaagcaa gcacaacaaa tgaagcaacg aagatggccg   2760
ggtagaatct actccatacc agcctacatt gtcttattag ttacctgcta ccacatatgg   2820
cccctcctcc ccttcctgct aacccgctc atccggctca tcctgctcgt cctcctctcc   2880
ccctcctcgt cctccccatc ttcaccctcc tcctactcct tctcctcgtc cttgtactcg   2940
tcctcgtcct cacccaacac aacgactcac ccaatttcct tgcatggcct tcga         2994
```

<210> SEQ ID NO 2
<211> LENGTH: 1265

```
<212> TYPE: DNA
<213> ORGANISM: Nannochloropsis

<400> SEQUENCE: 2
atgacatcct cccccaccagc ctcaccatct gcacctgaga atccctataa cctattgcca      60
cctaagcggc caaatccgca gtactggcgg tatgcaagcc tgaccgcttt cattctcatt     120
tgcttccaag ccccttcaag tgactcgtgg ggcaccgccc tccgccgcgc ctgctgggcg     180
gcgtactgga tgacctacct ggacacaagc tataaggatg gctcacgggc ctggccctgg     240
tttcagcgct taaggatctg gcgtttgtac tgcggctatt tacaggtgcg tgcatgtaag     300
agtaagggag ggagggagga aggaagagag gggtggtatt atgcattacc gaaggtcgat     360
caagcaagga gaatagattg agctcacgta ggaaatattc gattggtcag aaccaaaggt     420
atgtaggtgc tgttgtcatc gctatgtcct gctcatcgtt accatccgcc cactcatccc     480
ctgtctccct ctcttctttc ctccctccat cgcatcgacc aaagggcaaa gtaatttgta     540
cggtgcccct tggacccggca cagcaattca tcttcgcagc tcatcccccac ggcattggca     600 cctggaatca tttcctaacc atgactgacg gctgtcgctt cctctcctca tcctaccccc     660 gccccgcggct cgacctgggt gcgacggtac ttttcttcat ccccttctta aggaaattc     720 tgctctggct gggctgtgtg gatgctggag cgtccacggc tcacgcaatc ttggcgcggg     780
gctactcatc cctcatttac attggtggag aaaaggagca gattttaacg cagcgaggca     840
aagacatcgt ggtggtacgt ccccgcaagg gttttgcaa gctggccctg caacatgact     900
gccccatcgt acccgtctac gcgttgggg agaacgatct ctatcgcaca ttcaaccacc     960
tgaaggactt ccaactgtgg gtggccagca ccttaagct ggcttttcct ccttgttggg    1020
gcgtcccctt cctccccttc ctccctctgc cagtccccgt cacggtggtg atgggcgaac    1080
ccttgcggcc cagaacagga gaaggaaagg agggaagggc tggtggagaa aaaggagtga    1140
agcccacaag ggaggaggtg gacgagctgc acacccggta cgtggaggcc ctgcagaggt    1200
tgttcgacgc acacaagggc aggcacgggg ggaggagcga agaggccacc ttagtggtca    1260
ggtga                                                                1265

<210> SEQ ID NO 3
<211> LENGTH: 1542
<212> TYPE: DNA
<213> ORGANISM: Nannochloropsis

<400> SEQUENCE: 3
ttatactgat actttgcctg tccttaaacc ccgcctcgcg ccccccctccc ctccctcttc      60 cccttcttg ctctcctcct tttgctgctc ctttcccatc attcccactt tcgtgaactt     120
agcatcgaag gcatccacaa cccgctgccc aacgctggtt cccagcttca gcttttgtc     180 ggccgtaaag cggtagtgga taccgccgta gatacgggag taggctaggt cttcactcac     240
tgcagtcagc gagctgtact gcctcgtcac caccggtatg acatccgccg cttctgctgc     300
tgtaggtgct gcagttgttg cctgcaagct tcttttcccg gcttccaacc ctctcaccgt     360
gggtgtcgtc aagttgacgt ccagctggtc ggccgccttc tccgcccctc atcacccttt     420 ccctccccccc ctcgcctgcc gcagcacctc ataatcgcc tgccgtgca ccgcgtgggc     480 cgatggaaac tcgggcgtag gcggggtagc caacagcggg gtgaaatcag gcactgccgt     540
cagtatccca ccgttgccga ggggcagggc cgtcacgggc cgccaggtgc tgtaaaagta     600
tttgctgtcc atggaggcca cccgggcgtc taatcccgcc acggccgcca tagcatacac     660
gcgcgaggcc tccagcacgt ccatcttctc cgtgacgcgg cccactatcg caaagatgat    720
```

```
agcgtccggt tgctcacacc agaagaccgc gccctccgtg tccttcaaga gccgttcctt      780
ggacgtagcg ttgcccaccg atttcacctc gtagtatgcc tgcttgtagg cggccgtact      840
gaggcccggg gggggaggag tgcgcagctc ttgcggactg gtcagaatat agggcgtcac      900
ccacctccac tgctccgcgc cccccggcag aaacaagggc ggagtgggtc gccatttgcc      960
ggcatcggcc gtggagttgg cgccgaggta gggagggagg acggtggcgg ctccgtcgtt     1020
gctgcgagat gatagcacgg ccttgcccac tttaactcct atctctcggg cactgactac     1080
atcggcatta ttgtcgtcgc ctgattgggc agcgtataga gcgggagtc caacttgggc      1140
atccctgcg gcaaaaggg tctcaagggt gtgcttgccc gccccagcca aggcagcttg       1200
cagacagggc atgagagcgc gaagctgctc ctttgcggca gtaagcgatg aaacgttccg     1260
cgtcacaagc acctcgttga gggcctgcca ctgggcaagg tggaggatgg agaggatgcg     1320
gccgcctacc aggaggttgg caaggggggtt gaggggcttg ctgggttcgg cgccattgcg    1380
gagggtatgg cccaccatgg cttgcgtcac cagctcggac caaggatgga ggtgctcgtt     1440
ggccatggtg ggggttggcg tctcgaggaa aagggcaagg gcgaggagga ggaccgcgag     1500
gaggcgaggg atggaggaag gagaatgatg tgctggtggc at                        1542
```

<210> SEQ ID NO 4
<211> LENGTH: 319
<212> TYPE: PRT
<213> ORGANISM: Nannochloropsis

<400> SEQUENCE: 4

```
Met Ser Pro Gln Gly Glu Asp Gly Gly Pro Ala Asp Ser Thr Thr Thr
1               5                   10                  15

Arg Thr Thr Thr Ser Glu Ala Met Ala Met Pro Ala Gly Ala Ala Gly
            20                  25                  30

Thr Ala Ala Thr Ser Ala Ser Asp Ser Pro Ser Ser His Gln Asp Glu
        35                  40                  45

Gly Gly Gly Pro Thr Gln Thr Val His Arg Gly Pro His Pro Asp Ile
    50                  55                  60

His Asp Gln Gly Asp Lys Thr Lys Lys Lys Lys Arg Lys Asp
65                  70                  75                  80

Arg Lys Leu Gln Asn Glu Ser Glu Asp Gln Gln Gln Gln Asp Thr Asp
                85                  90                  95

Ser His Ala Ser Ser Arg Pro Thr Thr Pro Ile Asn Met Thr Pro Pro
            100                 105                 110

Arg Ser Ser His Ala Arg Ser Pro Phe Gly Ala Gly Ser Pro Tyr Glu
        115                 120                 125

His Thr Leu Thr Pro Ser Asn Ile Asp Ile Thr Val Leu Glu Gly Leu
    130                 135                 140

Ala Ser Gly Val Gly Ser Asn Asn Gly Gly Pro Ser Arg Asp Asn Thr
145                 150                 155                 160

Pro Ser Arg Ser Pro Ser Arg Arg Ser Arg His Ala Arg Arg Ala Lys
                165                 170                 175

Ile Ala Ala Thr Thr Lys Lys Arg Lys Ile Leu Gly Ser Phe Ile Leu
            180                 185                 190

Gly Ala Ile Phe Gly Met Ser Ile Leu Gly Trp Val Leu Arg His Lys
        195                 200                 205

Tyr Pro Gln Tyr Val Pro Ser Leu Ser Pro Asn Leu Asn Leu Asn Ile
    210                 215                 220

Ser Ala Val Leu Pro Ala Gly Phe Gly Leu Gly Leu Ser Ala Gly Glu
```

```
                    225                 230                 235                 240
Leu Asn Ser Thr Ile Leu Thr Asp Ile Tyr Gly Tyr Met Ser Trp Ala
                245                 250                 255

Ser Thr Pro Glu Thr Tyr Pro Gly Leu Gln Ala Ala Glu Lys Asn Tyr
            260                 265                 270

Ser Ala Lys Tyr Ser Ile Val Leu Ile Pro Gly Phe Val Thr Thr Gly
        275                 280                 285

Leu Glu Val Trp Gln Gly Glu Cys Ala Ser Ser Leu Phe Arg Ser
    290                 295                 300

Arg Leu Trp Gly Ala Val Ser Met Leu Gln Val Arg Thr Cys Thr
305                 310                 315

<210> SEQ ID NO 5
<211> LENGTH: 273
<212> TYPE: PRT
<213> ORGANISM: Nannochloropsis

<400> SEQUENCE: 5

Met Ser Cys Ser Ser Leu Pro Ser Ala His Ser Ser Pro Val Ser Leu
1               5                   10                  15

Ser Ser Phe Leu Pro Pro Ser His Arg Pro Lys Gly Lys Val Ile Cys
            20                  25                  30

Thr Val Pro Leu Asp Pro Ala Gln Gln Phe Ile Phe Ala Ala His Pro
        35                  40                  45

His Gly Ile Gly Thr Trp Asn His Phe Leu Thr Met Thr Asp Gly Cys
    50                  55                  60

Arg Phe Leu Ser Ser Ser Tyr Pro Arg Pro Arg Leu Asp Leu Gly Ala
65                  70                  75                  80

Thr Val Leu Phe Phe Ile Pro Phe Leu Lys Glu Ile Leu Leu Trp Leu
                85                  90                  95

Gly Cys Val Asp Ala Gly Ala Ser Thr Ala His Ala Ile Leu Ala Arg
            100                 105                 110

Gly Tyr Ser Ser Leu Ile Tyr Ile Gly Gly Glu Lys Glu Gln Ile Leu
        115                 120                 125

Thr Gln Arg Gly Lys Asp Ile Val Val Arg Pro Arg Lys Gly Phe
    130                 135                 140

Cys Lys Leu Ala Leu Gln His Asp Cys Pro Ile Val Pro Val Tyr Ala
145                 150                 155                 160

Phe Gly Glu Asn Asp Leu Tyr Arg Thr Phe Asn His Leu Lys Asp Phe
                165                 170                 175

Gln Leu Trp Val Ala Ser Thr Phe Lys Leu Ala Phe Pro Pro Cys Trp
            180                 185                 190

Gly Val Pro Phe Leu Pro Phe Leu Pro Leu Pro Val Pro Val Thr Val
        195                 200                 205

Val Met Gly Glu Pro Leu Arg Pro Arg Thr Gly Glu Gly Lys Glu Gly
    210                 215                 220

Arg Ala Gly Gly Glu Lys Gly Val Lys Pro Thr Arg Glu Glu Val Asp
225                 230                 235                 240

Glu Leu His Thr Arg Tyr Val Glu Ala Leu Gln Arg Leu Phe Asp Ala
                245                 250                 255

His Lys Gly Arg His Gly Gly Arg Ser Glu Glu Ala Thr Leu Val Val
            260                 265                 270

Arg

<210> SEQ ID NO 6
```

<211> LENGTH: 513
<212> TYPE: PRT
<213> ORGANISM: Nannochloropsis

<400> SEQUENCE: 6

```
Met Pro Pro Ala His His Ser Pro Ser Ser Ile Pro Arg Leu Leu Ala
1               5                   10                  15

Val Leu Leu Leu Ala Leu Ala Leu Phe Leu Glu Thr Pro Thr Pro Thr
            20                  25                  30

Met Ala Asn Glu His Leu His Pro Trp Ser Glu Leu Val Thr Gln Ala
        35                  40                  45

Met Val Gly His Thr Leu Arg Asn Gly Ala Glu Pro Ser Lys Pro Leu
    50                  55                  60

Asn Pro Leu Ala Asn Leu Leu Val Gly Gly Arg Ile Leu Ser Ile Leu
65                  70                  75                  80

His Leu Ala Gln Trp Gln Ala Leu Asn Glu Val Leu Val Thr Arg Asn
                85                  90                  95

Val Ser Ser Leu Thr Ala Ala Lys Glu Gln Leu Arg Ala Leu Met Pro
            100                 105                 110

Cys Leu Gln Ala Ala Leu Ala Gly Ala Gly Lys His Thr Leu Glu Thr
        115                 120                 125

Leu Leu Pro Ala Gly Asp Ala Gln Val Gly Leu Pro Ala Leu Tyr Ala
    130                 135                 140

Ala Gln Ser Gly Asp Asp Asn Asn Ala Asp Val Val Ser Ala Arg Glu
145                 150                 155                 160

Ile Gly Val Lys Val Gly Lys Ala Val Leu Ser Ser Arg Ser Asn Asp
                165                 170                 175

Gly Ala Ala Thr Val Leu Pro Pro Tyr Leu Gly Ala Asn Ser Thr Ala
            180                 185                 190

Asp Ala Gly Lys Trp Arg Pro Thr Pro Pro Leu Phe Leu Pro Gly Gly
        195                 200                 205

Ala Glu Gln Trp Arg Trp Val Thr Pro Tyr Ile Leu Thr Ser Pro Gln
    210                 215                 220

Glu Leu Arg Thr Pro Pro Pro Gly Leu Ser Thr Ala Ala Tyr Lys
225                 230                 235                 240

Gln Ala Tyr Tyr Glu Val Lys Ser Val Gly Asn Ala Thr Ser Lys Glu
                245                 250                 255

Arg Leu Leu Lys Asp Thr Glu Gly Ala Val Phe Trp Cys Glu Gln Pro
            260                 265                 270

Asp Ala Ile Ile Phe Ala Ile Val Gly Arg Val Thr Glu Lys Met Asp
        275                 280                 285

Val Leu Glu Ala Ser Arg Val Tyr Ala Met Ala Ala Val Ala Gly Leu
    290                 295                 300

Asp Ala Arg Val Ala Ser Met Asp Ser Lys Tyr Phe Tyr Ser Thr Trp
305                 310                 315                 320

Arg Pro Val Thr Ala Leu Pro Leu Gly Asn Gly Ile Leu Thr Ala
                325                 330                 335

Val Pro Asp Phe Thr Pro Leu Leu Ala Thr Pro Thr Pro Glu Phe
            340                 345                 350

Pro Ser Ala His Ala Val His Gly Glu Ala Ile Met Glu Val Leu Arg
        355                 360                 365

Gln Ala Arg Gly Gly Lys Gly Asp Glu Gly Ala Glu Lys Ala Ala
    370                 375                 380

Asp Gln Leu Asp Val Asn Leu Thr Thr Pro Thr Val Arg Gly Leu Glu
385                 390                 395                 400
```

Ala Gly Lys Arg Ser Leu Gln Ala Thr Thr Ala Ala Pro Thr Ala Ala
            405                 410                 415

Glu Ala Ala Asp Val Ile Pro Val Val Thr Arg Gln Tyr Ser Ser Leu
        420                 425                 430

Thr Ala Val Ser Glu Asp Leu Ala Tyr Ser Arg Ile Tyr Gly Gly Ile
    435                 440                 445

His Tyr Arg Phe Thr Ala Asp Lys Ser Leu Lys Leu Gly Thr Ser Val
    450                 455                 460

Gly Gln Arg Val Val Asp Ala Phe Asp Ala Lys Phe Thr Lys Val Gly
465                 470                 475                 480

Met Met Gly Lys Glu Gln Gln Lys Glu Ser Lys Lys Gly Glu Glu
                485                 490                 495

Gly Gly Glu Gly Gly Ala Arg Arg Gly Leu Arg Thr Gly Lys Val Ser
            500                 505                 510

Val

<210> SEQ ID NO 7
<211> LENGTH: 48
<212> TYPE: DNA
<213> ORGANISM: Artificial Sequence
<220> FEATURE:
<223> OTHER INFORMATION: Synthetic EP259 Primer

<400> SEQUENCE: 7
tccacacgat agtcaactcc accatctccg ttgtaaagtt ggagggct         48

<210> SEQ ID NO 8
<211> LENGTH: 24
<212> TYPE: DNA
<213> ORGANISM: Artificial Sequence
<220> FEATURE:
<223> OTHER INFORMATION: Synthetic P260 Primer

<400> SEQUENCE: 8
tcgaaggcca tgcaaggaaa ttgg                                    24

<210> SEQ ID NO 9
<211> LENGTH: 24
<212> TYPE: DNA
<213> ORGANISM: Artificial Sequence
<220> FEATURE:
<223> OTHER INFORMATION: Synthetic P119 Primer

<400> SEQUENCE: 9
ctgatcttgt ccatctcgtg tgcc                                    24

<210> SEQ ID NO 10
<211> LENGTH: 48
<212> TYPE: DNA
<213> ORGANISM: Artificial Sequence
<220> FEATURE:
<223> OTHER INFORMATION: Synthetic EP298 Primer

<400> SEQUENCE: 10
tccacacgat agtcaactcc accagtcatg gttggccatg attacgga          48

<210> SEQ ID NO 11
<211> LENGTH: 23
<212> TYPE: DNA
<213> ORGANISM: Artificial Sequence
<220> FEATURE:
<223> OTHER INFORMATION: Synthetic P299 Primer

```
<400> SEQUENCE: 11
atggactcgg tggcaaagct gaa                                          23

<210> SEQ ID NO 12
<211> LENGTH: 24
<212> TYPE: DNA
<213> ORGANISM: Artificial Sequence
<220> FEATURE:
<223> OTHER INFORMATION: Synthetic P119 Primer

<400> SEQUENCE: 12
ctgatcttgt ccatctcgtg tgcc                                         24
```